United States Patent

Harmon et al.

[11] Patent Number: 5,959,113
[45] Date of Patent: Sep. 28, 1999

[54] IMIDAZOL DERIVATIVES

[75] Inventors: Charles Stanford Harmon, Bloomfield, N.J.; Markus Kamber, Allschwil; Anna Krasso, Basel, both of Switzerland; Wolfgang Pirson, Weil am Rhein, Germany; Pierre-Charles Wyss, Muttenz, Switzerland

[73] Assignee: Hoffmann-La Roche Inc., Nutley, N.J.

[21] Appl. No.: 08/860,750

[22] PCT Filed: Dec. 1, 1995

[86] PCT No.: PCT/EP95/04741

§ 371 Date: Jun. 12, 1997

§ 102(e) Date: Jun. 12, 1997

[87] PCT Pub. No.: WO96/18626

PCT Pub. Date: Jun. 20, 1996

[30] Foreign Application Priority Data

Dec. 13, 1994 [CH] Switzerland .............................. 3768/94

[51] Int. Cl.⁶ .................... C07D 401/04; C07D 403/04; A61K 31/44; A61K 31/47
[52] U.S. Cl. .................... 546/268.1; 546/268.4; 544/358; 544/360; 544/366; 544/106; 544/111; 544/124; 514/89; 514/133; 514/235.8; 514/231.5; 514/235.5; 514/255
[58] Field of Search ..................... 544/111, 360, 544/365, 124; 546/268.1, 268.4; 514/89, 133, 231.5, 235.5, 235.8, 255

[56] References Cited

U.S. PATENT DOCUMENTS 3,772,441  11/1973  Lombardino ............................ 424/273
3,940,486  2/1976  Fitzi .................................. 424/263

FOREIGN PATENT DOCUMENTS 2010636  8/1990  Canada .
2221546  5/1972  European Pat. Off. .
0384349  8/1990  European Pat. Off. .
93/14081  7/1993  WIPO .
93/14082  7/1993  WIPO .
94/03427  2/1994  WIPO .
95/03297  2/1995  WIPO .
95/07922  3/1995  WIPO .

OTHER PUBLICATIONS

Gallagher et al., Bioorg. Med. Chem. Lett. (1995), 5 (11), pp. 1171–1176.
Kaufmann et al., Angew Chem. (1973), 85 (13), pp. 584–585.
Proc. Natl. Acad. Sci, 87, pp. 782–785 (1990).
Int. J. Biochem. 26, pp. 1203–1226 (1994).
Curr. Opin. Biotechnol. 6, pp. 657–661 (1995).
Ann. N. Y. Acad. Sci. 696, pp. 149–170 (1993).
Moore, et al. J. Endocrino. 88, pp. 293–299 (1981).
Chapman & Hardy, J. Biol. Sci. 41, pp. 261–268 (1988).
Philpott, et al. J. Cell Sci. 97, pp. 463–471 (1990).
Thom. et al. Biochem. J. 168, pp. 187–194 (1977).
U. Kikkawa et al., Methods Enzymol. 99, pp. 288–298 (1983).
Buhl et al., J. Invest. Dermatol. 92, pp. 315–320 (1989).

*Primary Examiner*—Jose' G. Dees
*Assistant Examiner*—Sabiha N. Qazi
*Attorney, Agent, or Firm*—George W. Johnston; Patricia S. Rocha-Tramaloni

[57] ABSTRACT

This invention relates to novel imidazole derivatives of formula a

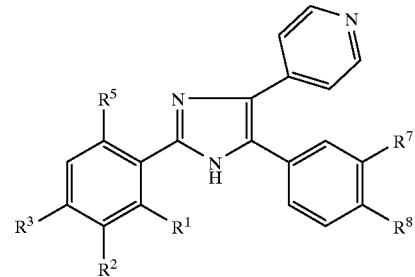

and pharmaceutically acceptable salts of these compounds, wherein $R^1$, $R^2$, $R^3$, $R^5$, $R^7$ and $R^8$ are as disclosed herein. These compounds are protein kinase inhibitors useful in the treatment of atherosclerosis, psoriasis, alopecia, and tumors.

19 Claims, No Drawings

IMIDAZOL DERIVATIVES

This application is a 371 of PCT/EP95/04741 filed Dec. 12, 1995.

The invention is concerned with novel imidazole derivatives of the general formula

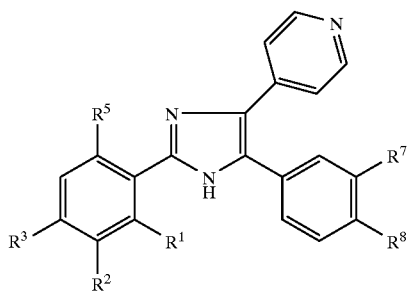

(I)

wherein $R^1$ signifies lower-alkyl or halogen, $R^2$ signifies hydrogen, hydroxy, nitro, lower-alkoxycarbonyl, di(lower-alkyl) amino-lower-alkyl, morpholino-lower-alkyl or 4-methylpiperazinyl-lower-alkyl, $R^3$ signifies hydrogen or lower-alkyl, $R^5$ signifies amino or lower-alkyl, $R^7$ signifies hydrogen or lower-alkyl, and $R^8$ signifies hydrogen or halogen, and pharmaceutically usable salts thereof.

The term "lower-alkyl" used here, alone or in combination, signifies a straight-chain or branched alkyl group with 1–6 C atoms such as methyl, ethyl, n-propyl, isopropyl, n-butyl, sec.-butyl, isobutyl, tert. butyl, n-pentyl and n-hexyl. The term "halogen" or "halo" embraces fluorine, chlorine, bromine and iodine.

Methyl and isopropyl are preferred lower-alkyl groups. Chlorine is a preferred halogen.

Examples of preferred compounds of formula I are:

4-[5-(4-Chlorophenyl)-2-(2,4,6-trimethylphenyl) imidazol-4-yl]pyridine,

4-[5-(3-methylphenyl)-2-(2,4,6-trimethylphenyl) imidazol-4-yl]pyridine, 3-chloro-2-[4-(4-chlorophenyl)-5-pyridin-4-yl-imidazol-2-yl]phenylamine, 4-[5-(4-chlorophenyl)-2-(2,6-diisopropylphenyl) imidazol-4-yl]pyridine, methyl 3-[5-(4-chlorophenyl)-4-pyridin-4-yl-imidazol-2-yl]-2,4,6-trimethylbenzoate, 4-[3-[5-(4-chlorophenyl)-4-pyridin-4-yl-imidazol-2-yl]-2,4,6-trimethylbenzyl]morpholine,

[3-[5-(4-chlorophenyl)-4-pyridin-4-yl-imidazol-2-yl]-2,4,6-trimethylbenzyl]dimethylamine, 1-[3-[5-(4-chlorophenyl)-4-pyridin-4-yl-imidazol-2-yl]-2,4,6-trimethylbenzyl]-4-methylpiperazine, 4-[5-(4-chlorophenyl)-2-(2,4,6-trimethyl-3-nitrophenyl)-imidazol-4-yl]pyridine, 3-[5-(4-chlorophenyl)-4-pyridin-4-yl-imidazol-2-yl]-2,4,6-trimethylphenol and 4-[5-(4-fluorophenyl)-2-(2-bromo-6-methylphenyl)-imidazol-4-yl]-pyridine.

The compounds of formula I which contain acidic functions can form pharmaceutically usable salts with bases such as alkali metal hydroxides (e.g. sodium hydroxide and potassium hydroxide), alkaline earth metal hydroxides (e.g. calcium hydroxide and magnesium hydroxide) and ammonium hydroxide and the like. The compounds of formula I which contain basic functions can form pharmaceutically usable salts with acids. As such salts there come into consideration not only salts with inorganic acids such as hydrochloric acid or hydrobromic acid, sulphuric acid, nitric acid and phosphoric acid, but also salts with organic acids such as acetic acid, tartaric acid, succinic acid, fumaric acid, maleic acid, malic acid, salicylic acid, citric acid, methanesulphonic acid, p-toluenesulphonic acid etc.

The present invention is accordingly concerned with compounds of formula I and their pharmaceutically usable salts per se and for use as therapeutically active substances, a process for the manufacture of these compounds and their salts, medicaments which contain these compounds or salts and the production of these medicaments and the use of the compounds and their salts for the control of illnesses, especially hyperproliferative disorders such as atherosclerosis, psoriasis and tumours and for the treatment of alopecia, or for the production of a medicament for the treatment and prevention of such disorders.

The pharmacological activity of the compounds in accordance with the invention can be determined on the basis of their activity as protein kinase inhibitors and inhibitors of HaCaT-cell proliferation. In particular, the compounds in accordance with the invention are selective inhibitors of epidermal growth factor receptor (EGF-R) tyrosine kinase.

EGF-R plays a rôle in the development and metastation of certain human malignant diseases such as breast cancer, cancer of the liver and cancer of the prostate.

For all known functions and activities of EGF-R its tyrosine kinase activity is a determining factor. The inhibition of this enzymatic activity by the compound of formula I can therefore be looked upon as a measurement for the efficacy in the therapeutic treatment of EGF-R-mediated hyperproliferative diseases such as certain forms of cancer and psoriasis.

In contrast to the stimulating rôle of the EGF receptor in keratinocyte proliferation, in vitro and in vivo studies show that the activation of this receptor is a negative regulator of hair follicle activity. Thus, the injection of EGF inhibits hair growth in newborn mice (Moore et al., J. Endocrinol 88, 293 [1981]) and sheep (Chapman & Hardy from J. Biol. Sci. 41, 261 [1988]) and the treatment of cultured human hair follicles with EGF induces a catagen-like state (Philpott et al., J. Cell Sci. 97, 463 [1990]) with inhibition of hair fibre production. These findings suggest that inhibition of EGF-R tyrosine kinase stimulates hair growth and lengthens the duration of the anagen phase of the hair cycle in vivo.

The biological activity of the compounds in accordance with the invention was tested in various test models which are described hereinafter.

Tyrosine protein kinases

Inhibition of EGF-receptor Tyrosine Kinase

The activity of EGF-receptor tyrosine kinase is determined by measuring the transfer of $^{32}$P-labelled phosphate from $^{32}$P-γ-ATP (10 μM) to the substrate RR-scr peptide* (0.75 mM). A membrane fraction from human A431 cells is used as the enzyme. It is isolated according to Thom et al., Biochem. J. 168, 187 (1977) and stored at −75° C. (4–6 mg protein/ml). The compounds are tested in 10% DMSO in a concentration of 0.001–100 μM. The incubation is carried out at 30° C. for a period of 30 minutes in Tris buffer (25 mM, pH 7.4) which contains magnesium acetate (30 mM), sodium vanadate (0.5 mM), 0.5% BSA and 0.05% Triton X-100. The membranes are pre-incubated with 2 μM of EGF at 4° C. for 90 minutes. The test is started by adding the enzyme (2 μg of membrane protein) and terminated by adding ice-cold KH$_2$PO$_4$ (1M, pH 3.0). After centrifugation the labelled peptide is separated from excess ATP in the supernatant by reversed phase HPLC. The peptide fraction is collected and the radioactivity is measured in a standard β-counter or on-line with a radiometer (Berthold). The inibitory activity of the test compound is expressed as the mikromolar concentration which is required for 50% inhibition (IC$_{50}$ [μM]).

*RR-src peptide=[Arg-Arg-Leu-Ile-Glu-Asp-Ala-Glu-Tyr-Ala-Ala-Arg-Gly]

Inhibition of p56$^{lck}$ tyrosine kinase

The activity of p56$^{lck}$ tyrosine kinase is determined by measuring the transfer of $^{32}$P-labelled phosphate from $^{32}$P-γ-ATP (10 μM) to the substrate RR-src peptide (0.75 mM). Human recombinant p56$^{lck}$ (expressed in *E. coli*) is used as the enzyme.

It is purified from the soluble fraction by means of a monoclonal antibody column and stored at −75° C. The compounds are tested in 10% DMSO in a concentration of 0.001–100 μM, The incubation is carried out at 30° C. for a period of 30 minutes in HEPES buffer (50 mM, pH 6.9) which contains manganese chloride (11 mM) and 0.5% BSA. The test is started by adding the enzyme and terminated by adding ice-cold KH$_2$PO$_4$ (1M, pH 3.0). After centrifugation the radiolabelled peptide is separated from excess ATP in the supernatant by reversed phase HPLC. The peptide fraction is collected and the radioactivity is determined in a standard β- counter or on-line with a radiometer (Berthold). The inhibitory activity of the test compound is expressed as the micromolar concentration which is required for 50% inhibition (IC$_{50}$ [μM]).

Serine/threonine protein kinases

Inhibition of cAMP-dependent protein kinase (PKA)

The activity of PKA is measured by measuring the transfer of $^{32}$P-labelled phosphate from $^{32}$P-γ-ATP (10 μM) to the substrate histone H1 (333 μg/ml) using partially purified PKA from hog brain (DEAE chromatography according to U. Kikkawa et al., Methods Enzymol. 99, 288, 1983). PKA is activated by 2 μM of cAMP in Tris HCl buffer (20 mM, pH 7.4). The compounds are tested in DMSO/buffer at a concentration of 0.001–100 μM. The test is started by adding the enzyme, takes 2 minutes at 32° C. and is terminated by adding 20% trichloroacetic acid (containing 1% SDS and 1% sodium pyrophosphate). The precipitated protein, which contains the radiolabelled histone, is separated from excess ATP by filtration through a nitrocellulose membrane filter. The radioactivity on the filter is determined in a scintillation counter. The inhibitory activity of the test compounds is expressed as the micromolar concentration which is required for 50% inhibition (IC$_{50}$ [μM]).

Inhibition of protein kinase C (PKC)

The activity of PKC is measured by measuring the transfer of $^{32}$P-labelled phosphate from $^{32}$P-γ-ATP (10 μM) to the substrate histone H1 (200 μg/ml) using partially purified PKC from hog brain (DEAE chromatography according to U. Kikkawa et al., Methods Enzymol. 99, 288, 1983). PKC is activated by phospholipid vesicle prepared by sonicating a mixture of 0.05 ml of phosphatidylserine (10 mg/ml) and 0.005 ml of diolein (10 mg/ml) in 5 ml of Tris HCl buffer (20 mM, pH 7.4). The compounds are tested in DMSO/buffer at a concentration of 0.001–100 μM. The test is started by adding the enzyme, takes 2 minutes at 32° C. and is terminated by adding 20% trichloroacetic acid (containing 1% SDS and 1% sodium pyrophosphate). The precipitated protein with the labelled histone is separated from excess ATP by filtration over a nitrocellulose membrane filter. The radioactivity on the filter is measured in a scintillation counter. The inhibitory activity of the test compound is expressed as the micromolar concentration which is required for 50% inhibition (IC$_{50}$ [μM]).

Inhibition of HaCaT cell proliferation

HaCaT is a spontaneous immortalized human keratinoycte cell line (Boukamp et al. 1988) which has been used many times as a model system for hyperproliferative keratinoyctes. The incorporation of [$^3$H]-thymidine was used to quantify the growing cells in the S phase of the cell cycle. The cells were cultivated with a 3:1 mixture of DMEM/F12 medium which had been supplemented with 5% FCS, EGF (10 μg/l), hydrocortisone (400 μg/l), cholera toxin (8.5 μg/l), insulin (5 μg/l), L-glutamine (2 mM) and penicillin/streptomycin. 200 μl of medium were placed in microtitre plates such that each sample contained 5000 cells. The test compounds were added in serial dilutions in the range of 1×10$^{-8}$ M to 1×10$^{31}$ $^5$ M at the beginning of the cultivation. The cells were incubated at 37° C. for 48 hours. For the last 6 hours [$^3$H]-thymidine was added (1 mCi/sample). After digesting the cells with trypsin the amount of incorporated radioactivity was quantified with a liquid scintillation counter.

The inhibition of selected protein kinases in vitro and the inhibition of cell proliferation in HaCaT-cells by these compounds are set forth in the following Table.

| | IC$_{50}$ (μM) | | | | |
|---|---|---|---|---|---|
| | Isolated enzyme | | | | Cells |
| Example | EGF-R | p56$^{lck}$ | PCK | PKA | HaCaT |
| 1 | 0.34 | 2.2 | >100 | 6.3 | 2 |
| 4 | 0.80 | 6.0 | >100 | 190 | 2 |
| 16 | 0.31 | 2.2 | n.t. | n.t. | 0.8 |
| 7 | 0.13 | 3.1 | 100 | 0.47 | 3.5 |
| 9 | 0.14 | 3.8 | 80 | 6.0 | 0.23 |
| 11 | 0.26 | 5.1 | >100 | 43 | 0.1 |
| 12 | 0.05 | 1.65 | 7.0 | 5.0 | 0.57 |
| 13 | 0.05 | 1.8 | 37 | 1.5 | 0.1 |
| 15 | 0.78 | 4.95 | n.t. | n.t. | 0.67 |
| 18 | 0.29 | 14 | 23 | 1.8 | 2 | n.t.: not tested

Stimulation of cell proliferation in cultured mouse hair follicles

Mouse hair follicles are isolated and cultured according to the method described by Buhl et al., J. Invest. Dermatol. 92, 315 (1989). Whisker parts are removed from CD-1 mice aged 4 days and the hair follicles are carefully separated from surrounding tissue under the microscope. Hair follicles are cultured in M199 medium which contains 20% FBS and the cell proliferation is determined from the incorporation of [$^3$H]-thymidine in DNA. The test compounds are dissolved in DMSO and added in serial dilutions in the range of 1×10$^{-8}$ to 1×10$^{-6}$ M at the beginning of the cultivation. After 1 day 5 μCi/ml of [$^3$H]-thymidine are added to the culture medium and the follicles are incubated for a further 3 days. The hair follicles are then washed with phosphate-buffered saline solution in order to remove non-incorporated radioactivity and the DNA is solubilized by incubation with alkali overnight. The radioactivity incorporated into the follicular DNA is then measured using a liquid scintillation counter.

The incubation of mouse hair follicles with the compound of Example 1 results in a stimulation of the cell proliferation with a maximum DNA synthesis value of 211±17% (compared with controls) at a concentration of 0.3 μM. The concentration which resulted in a half-maximum stimulation of the DNA synthesis (EC$_{50}$ value) was 0.1 μM. The activity of the compound of Example 1 in this culture system exceeded that of known hypotrichotic agents. For example, minoxidil stimulates hair follicle DNA synthesis to 160±15% (compared with controls) and has a EC$_{50}$ value of 200 μM.

In accordance with the invention the compounds of formula I and their pharmaceutically usable salts can be manufactured in accordance with the invention by reacting a diketone of the general formula

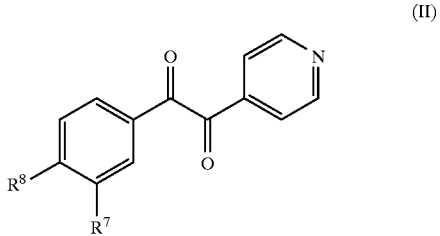

(II)

wherein $R^7$ and $R^8$ have the above significance, with an aldehyde of the general formula

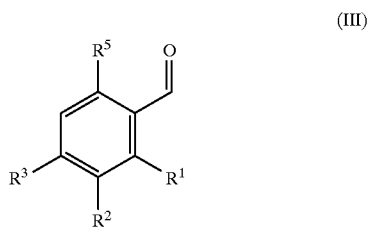

(III)

wherein $R^1$, $R^2$, $R^3$ and $R^5$ have the significance given above and wherein a hydroxy group in a compound of formula III can be present in protected form,
in the presence of ammonia, cleaving off a hydroxy protecting group which may be present and, if desired, functionally modifying reactive groups present in a compound of formula I obtained and, if desired, converting a compound of formula I into a pharmaceutically usable salt.

The reaction of a diketone of formula II with an aldehyde of formula III and with ammonia can be carried out in a manner known per se. For example, a diketone of formula II can be reacted with an aldehyde of formula III and with ammonium acetate (a reagent which liberates ammonia) in an organic acid such as acetic acid at an elevated temperature, e.g. at about 50 to about 100° C.

A hydroxy group in a compound of formula III can be present in the reaction in accordance with the invention in protected form, for example as a benzyl ether, which can be removed from the reaction product in a manner known per se, in the case of the benzyl ether by e.g. catalytic hydrogenation.

The diketones of formula II and aldehydes of formula III are known or can be prepared in a manner known per se as described in the Examples or in analogy thereto.

Functional modification of reactive groups can comprise e.g. the saponification of ester groups, the reduction of nitro groups to amino groups and the alkylation of amino groups. These functional modifications can be carried out in a manner known per se, e.g. as described in the Examples or in analogy thereto.

Acidic compounds of formula I can be converted into pharmaceutically usable salts by treatment with bases and basic compounds of formula I can be converted into pharmaceutically usable salts by treatment with acids. Such reactions can be carried out in a manner known per se.

The compounds of formula I and their salts can be used as medicaments, e.g. in the form of pharmaceutical preparations.

The medicaments can be administered enterally, parenterally or topically. Medicaments in the form of tablets, capsules, drageés, syrups, suspensions, solutions and suppositories are e.g. suitable for enteral administration. Medicaments in the form of infusion or injection solutions are suitable for parenteral administration.

The dosages in which the preparations are administered can vary according to the mode of use and route of use as well as according to the requirements of the patient.

In the case of the oral administration of the compounds in accordance with the invention there come into consideration in the case of adults dosages of about 0.1–100 mg/kg, preferably 0.5–50 mg/kg, per day.

The preparations can be administered in one or more doses. Capsules containing about 5–500 mg of active ingredient comprise a preferred administration form.

The preparations can contain inert or pharmacodynamically active additives. Tablets or granulates e.g. can contain a series of binders, fillers, carriers or diluents. Liquid preparations can be present, for example, in the form of a sterile water-miscible solutions. Capsules can contain a filler or thickener in addition to the active ingredient. Furthermore, flavour-improving additives as well as substances usually used as preservatives, stabilizers, moisturizers and emulsifiers as well as salts for varying the osmotic pressure, buffers and other additives can be present.

The previously mentioned carriers and diluents can comprise organic or inorganic substances, e.g. water, gelatine, lactose, starch, magnesium stearate, talc, gum arabic, polyalkylene glycols and the like. It is a prerequisite that all adjuvants used in the production of the preparations are non-toxic.

For topical application the active ingredients are conveniently used in the form of salves, tinctures, creams, solutions, lotions, sprays, suspensions, gels and the like. Salves and creams as well as solutions are preferred. These preparations adapted for topical application can be produced by mixing the process products as active ingredients with non-toxic, inert solid or liquid carriers which are suitable for topical treatment and which are customary in such preparations.

For topical application there are conveniently suitable about 0.1–10%, preferably 0.3–2%, solutions as well as about 0.1–10%, preferably about 0.3–2%, salves and creams.

If desired, an antioxidant, e.g. tocopherol, N-methyl-γ-tocopheramine as well as t-butyl-hydroxyanisole or t-butyl-hydroxtolune, can be admixed with the preparations.

The following Examples illustrate the invention in more detail.

EXAMPLE 1

A mixture of 12.3 g of 1-(4-chlorophenyl)-2-pyridin-4-yl-ethanedione and 7.4 g of 2,4,6-trimethylbenzaldehyde in 125 ml of acetic acid containing 40 g of ammonium acetate was stirred at 100° C. for 2 hours, then left to cool to room temperature. The mixture was poured into a mixture of 300 ml of ice-water and 200 ml of concentrated ammonia solution and the mixture was extracted three times with ethyl acetate. After drying over anhydrous magnesium sulphate the solvent was evaporated. The residue was purified by chromatography on silica gel with dichloromethane/methanol (9:1) and crystallized from ethyl acetate to yield 6.7 g of 4-[5-(4-chlorophenyl)-2-(2,4,6-trimethyphenyl) imidazol-4-yl]pyridine, m.p. 275° C.

EXAMPLES 2–17

The following compounds were prepared in analogy to Example 1:

2. 4-[5-(4-fluorophenyl)-2-(2,4,6-trimethylphenyl)imidazol-4-yl]pyridine, m.p. 252–254° C. (diethyl ether),
3. 4-[5-(4-chlorophenyl)-2-(2,6-dimethylphenyl)imidazol-4-yl]pyridine, m.p. 290–292° C. (ethyl acetate/hexane),
4. 4-[5-(3-methylphenyl)-2-(2,4,6-trimethylphenyl)imidazol-4-yl]pyridine, m.p. 251–253° C. (diethyl ether),
5. 4-[5-(4-chlorophenyl)-2-(2-chloro-6-methylphenyl)-imidazol-4-yl]pyridine, m.p. >260° C. (acetone),
6. 4-[5-(4-chlorophenyl)-2-(2-bromo-6-methylphenyl)-imidazol-4-yl]pyridine, m.p. >260° C. (acetone/hexane),
7. 4-[5-(4-chlorophenyl)-2-(2,6-diisopropylphenyl)imidazol-4-yl]pyridine, m.p. >260° C. (acetone/hexane),
8. 4-[5-(4-fluorophenyl)-2-(2-bromo-6-methylphenyl)-imidazol-4-yl]pyridine, m.p. >260° C. (dichloromethane),
9. methyl 3-[5-(4-chlorophenyl)-4-pyridin-4-yl-imidazol-2-yl]2,4,6-trimethylbenzoate, m.p. 228° C. (ethyl acetate/isopropyl ether),
10. 4-[5-(4-chlorophenyl)-2-(2,6-dimethyl-3-nitrophenyl)-imidazol-4-yl]pyridine, m.p. 295–298° C. (ethyl acetate/hexane),
11. 4-[3-[5-(4-chlorophenyl)-4-pyridin-4-yl-imidazol-2-yl]-2,4,6,-trimethylbenzyl]morpholine, m.p. 239–240° C. (ethyl acetate),
12. [3-[5-(4-chlorophenyl)-4-pyridin-4-yl-imidazol-2-yl]-2,4,6,-trimethylbenzyl]dimethylamine, m.p. 222° C. (acetonitrile),
13. 1-[3-[5-(4-chlorophenyl)-4-pyridin-4-yl-imidazol-2-yl]-2,4,6,-trimethylbenzyl]-4-methylpiperazine, m.p. 280° C. (ethyl acetate),
14. 3-[5-(4-chlorophenyl)-4-pyridin-4-yl-imidazol-2-yl]-2,4-dimethylphenol, m.p. >300° C. (ethanol),
15. 4-[5-(4-chlorophenyl)-2-(2,4,6-trimethyl-3-nitrophenyl)-imidazol-4-yl]pyridine, m.p. 295–299° C. (methanol/ethyl acetate),
16. 3-[5-(4-chlorophenyl)-4-pyridin-4-yl-imidazol-2-yl]-2,4,6,-trimethylphenol, m.p. >300° C. (ethanol),
17. (2RS,6RS)- and (2R,6S)-4-[3-[5-(4-chlorophenyl)-4-pyridin-4-yl-imidazol-2-yl]-2,4,6-trimethylbenzyl]-2,6-dimethylmorpholine, m.p. 163–170° C. (ethyl acetate).

EXAMPLE 18

A solution of 0.2 g of 4-[5-(4-chlorophenyl)-2-(2-chloro-6-nitrophenyl) imidazol-4-yl]pyridine in 20 ml of methanol was hydrogenated in the presence of 0.1 g of 10% palladium/charcoal for 2 hours. The catalyst was filtered off and the solution was evaporated to dryness. Recrystallization from ethyl acetate yielded 0.1 g of 3-chloro-2-[5-(4-chlorophenyl)-4-pyridin-4-yl-imidazol-2-yl]phenylamine, m.p. 220–222° C.

The starting materials which are used in Examples 1–18, the preparation of which has not hitherto been described, can be prepared as described hereinafter or in analogy thereto:

A. Ethanone derivatives (compounds of formula II)

1-(4-Chlorophenyl)-2-pyridin-4-yl-ethanedione (i) 19.4 g of 4-pyridylmethyl isocyanide were added dropwise at −5° C. while stirring to a solution of 37.8 g of potassium tert-butylate in 400 ml of tetrahydrofuran. The mixture was then treated with 23.1 g of 4-chlorobenzaldehyde and stirred at −5° C. for a further 2 hours. Thereafter, 19.7 g of acetic acid were added dropwise at 0° C. while stirring and the solid was filtered off. The residue was chromatographed on silica gel with dichloromethane/methanol (95:5) as the eluent and recrystallized from dichloromethane/hexane. 25.0 g of (E/Z)-N-[2-(4-chlorophenyl)-1-pyridin-4-yl-vinyl] formamide, m.p. 155–156° C., were obtained.

(ii) A solution of 39.0 g of (E/Z)-N-[2-(4-chlorophenyl)-1-pyridin-4-yl-vinyl]formamide in 430 ml of methanol was treated at 0° C. with 112 ml of concentrated hydrochloric acid. The mixture was stirred at 32–34° C. for 16 hours. The mixture was then cooled to 0° C. and added dropwise while stirring at 0° C. to a solution of 82.2 g of potassium hydroxide in 100 ml of water. The solid was filtered off and recrystallized from dichloromethane/hexane. 25.0 g of 1-(4-chlorophenyl)-2-pyridin-4-yl-ethanone, m.p. 85–86° C., were obtained.

(iii) A solution of 25 g of 1-(4-chlorophenyl)-2-pyridin-4-yl-ethanone in 285 ml of dioxan was treated with 20 g of selenium dioxide. The mixture was stirred at 100° C. for 1 hour and filtered. The solvent was evaporated and the residue was dissolved in dichloromethane. The solution was washed three times with water, dried over anhydrous magnesium sulphate and evaporated. The residue was dissolved in ethyl acetate, the solution was filtered over silica gel and evaporated to yield 23.7 g of 1-(4-chlorophenyl)-2-pyridin-4-yl-ethanedione, m.p. 119–120° C.

B. Benzaldehyde derivatives (compound of formula III)

2-Bromo-6-methylbenzaldehyde (i) A solution of 9.52 g of (2-bromobenzylidene) phenylamine in 150 ml of acetic acid was treated with 7.9 g of palladium(II) acetate. The mixture was heated to reflux for 1 hour, then poured into 150 ml of water and extracted three times with dichloromethane. The combined organic extracts were washed with water, dried over anhydrous magnesium sulphate and evaporated to dryness. The residue was chromatographed on silica gel with dichloromethane/methanol (99:1) as the eluent and yielded 10.3 g of bis[acetato(3-bromo-2-phenyliminomethyl-phenyl)palladium](Pd-Pd), m.p. 199–200° C.

(ii) A solution of 10.3 g of bis[acetato(3-bromo-2-phenyliminomethylphenyl)palladium](Pd-Pd) in 80 ml of dichloromethane and 80 ml of acetone was treated with 90 ml of saturated sodium chloride solution while stirring. After 10 minutes the solid was filtered off and yielded 6.1 g of bis[chloro(3-bromo-2-phenyliminomethylphenyl) palladium](Pd-Pd), m.p. 280–282° C.

(iii) A solution of 6.1 g of bis[chloro(3-bromo-2-phenylimino-methylphenyl)palladium](Pd-Pd) in 225 ml of absolute benzene was treated with 7.9 g of triphenylphosphine under argon. Thereafter, the mixture was stirred at room temperature for a further 30 minutes. 12.5 ml of a 1.6M solution of methyllithium in diethyl ether was added dropwise at 0 C. while stirring and the mixture was thereafter stirred at room temperature for 1 hour. The mixture was then treated at 0° C. with 225 ml of 1N hydrochloric acid, filtered and the solid was washed with diethyl ether. The combined organic extracts were washed twice with water, dried over anhydrous magnesium sulphate and evaporated to dryness. The residue was chromatographed on silica gel with hexane/ethyl acetate (98:2) as the eluent and yielded 0.7 g of 2-bromo-6-methylbenzaldehyde, m.p. 48–49° C.

2,6-Diisopropylbenzaldehyde 6.8 ml of a 1.6M solution of butyllithium in hexane was added dropwise at −78° C. while stirring to a solution of 2.6 g of 2-bromo-1,3-diisopropylbenzene in 16 ml of tetrahydrofuran. The mixture was stirred at the same temperature for 30 minutes and thereafter treated with a solution of 1.3 g of N-formylpiperdine in 1.5 ml of tetrahydrofuran. Thereafter, the mixture was left to warm to room temperature over a period of 6 hours. The mixture was cooled to 0° C. and treated with 12 ml of 3N hydrochloric acid. The aqueous solution was extracted four times with diethyl ether and the combined organic extracts were washed with saturated sodium chloride solution, dried over anhydrous magnesium sulphate and evaporated to dryness. The residue was chromatographed on silica gel with dichloromethane as the eluent and yielded 1.07 g of 2,6-diisopropylbenzaldehyde as an oil.

2,6-Dimethyl-3-nitrobenzaldehyde 2 g of 2,6-dimethylbenzaldehyde were added at room temperature over a period of 15 minutes to a mixture of 20 ml of concentrated nitric acid and 10 ml of acetic acid. Thereafter, the mixture was stirred at room temperature for 5 minutes and poured on to ice-water. The mixture was stirred for a further 5 minutes, filtered and the residue was dissolved in dichloromethane. After drying over anhydrous magnesium sulphate the solvent was evaporated. The residue was chromatographed on silica gel with hexane/ethyl acetate as the eluent and yielded 1.23 g of 2,6-dimethyl-3-nitrobenzaldehyde, m.p. 54–57° C. (from hexane), and 0.33 g of 2,6-dimethyl-3,5-dinitrobenzaldehyde, m.p. 119–122° C. (from toluene/hexane).

2,4,6-Trimethyl-3-morpholin-4-yl-methylbenzaldehyde

A solution of 0.98 g of 3-chloromethyl-2,4,6-trimethylbenzaldehyde in 20 ml of acetonitrile was treated with 0.87 ml of morpholine. The mixture was stirred at room temperature for 4 hours and thereafter filtered. The solvent was evaporated and the residue was dissolved in ethyl acetate. The solution was washed twice with water, dried over anhydrous magnesium sulphate and evaporated to dryness. Distillation of the residue yielded 1.05 g of 2,4,6-trimethyl-3-morpholin-4-yl-methylbenzaldenhyde, b.p. 150° C./0.3 Torr.

3-Dimethylaminomethyl-2,4,6-trimethylbenzaldehyde

3-Dimethylaminomethyl-2,4,6-trimethylbenzaldehyde, b.p. 150° C./0.3 Torr, was prepared in analogy to the procedure described above for the preparation of 2,4,6-trimethyl-3-morpholin-4yl-methylbenzaldehyde morpholin-4-yl-methylbenzaldehyde.

2,4,6-Trimethyl-3-(4-methylpiperazin-1-yl-methyl)-benzaldehyde 2,4,6-Trimethyl-3-(4-methylpiperazin-1-yl-methyl)-benzaldehyde, m.p. 90° C. (from acetonitrile), was prepared in analogy to the manner described above for the preparation of 2,4,6-trimethyl-3-morpholin-4-yl-methylbenzaldehyde.

3-Hydroxy-2,6-dimethylbenzaldehyde (i) A solution of 2.8 g of 2,6-dimethyl-3-nitrobenzaldehyde in 150 ml of toluene was treated with 5 ml of ethylene glycol and 20 mg of p-toluenesulphonic acid. The mixture was heated to reflux for 18 hours, with the water being separated using a separator. The mixture was left to cool to room temperature and was washed twice with water. After drying over anhydrous magnesium sulphate the solvent was evaporated and the crystalline residue was crystallized from hexane. 3.0 g of 2-(2,6-dimethyl-3-nitrophenyl)-1,3-dioxolane, m.p. 69–71° C., were obtained.

(ii) A solution of 2.7 g of 2-(2,6-dimethyl-3-nitrophenyl)-1,3-dioxolane in 30 ml of ethyl acetate was hydrogenated in the presence of 0.2 g of platinum oxide for 45 minutes. The catalyst was filtered off and the solution was concentrated to a crystalline residue. Recrystallization from hexane yielded 2.35 g of 2-(3-amino-2,6-dimethylphenyl)-1,3-dioxolane, m.p. 100–103° C.

(iii) A solution of 0.73 g of sodium nitrite in 2 ml of water was added at 0° C. over a period of 15 minutes while stirring to a suspension of 2.0 g of 2-(3-amino-2,6-dimethylphenyl)-1,3-dioxolane in 1.9 ml of concentrated sulphuric acid and 5.5 ml of water.

Thereafter, the mixture was stirred at room temperature for 15 minutes and then added while stirring over a period of 5 minutes at 110° C. to a mixture of 1 ml of concentrated sulphuric acid and 15 ml of water. The mixture was heated to reflux while stirring for 1 hour, then left to cool to room temperature, filtered and washed with water to yield 1.55 g of 3-hydroxy-2,6-dimethylbenzaldehyde, m.p. 159–165° C. (from isopropyl ether).

3-Diethylaminomethyl-2,4,6-trimethylbehzaldehyde

3-Diethylaminomethyl-2,4,6-trimethylbenzaldehyde, b.p. 200° C./0.2 Torr, was prepared in analogy to the procedure described for the synthesis of 2,4,6-trimethyl-3-morpholin-4-yl-methlbenzaldehyde.

(2RS,6RS)- and (2R,6S)-3-(2,6-dimethylmorpholin-4-yl-methyl)-2,4,6-trimethylbenzaldehyde (2RS,6RS)- and (2R,6S)-3-(2,6-dimethylmorpholin-4-yl-methyl)-2,4,6-trimethylbenzaldehyde, m.p. 130° C. (hexane), was prepared in analogy to the procedure described above for the synthesis of 2,4,6-trimethyl-3-morpholin-4-yl-methyl-benzaldehyde.

Examples A–E illustrate the production of pharmaceutical preparations.

Example A

Hard gelatine capsules can be produced as follows:

| Ingredient | mg/capsule |
| --- | --- |
| 1. Spray-dried powder containing 75% compound I | 20 |
| 2. Sodium dioctylsulphosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 120 |

The spray-dried powder, which is based on the active ingredient, gelatine and microcrystalline cellulose and which has an average active ingredient particle size of <1μ (measured using autocorrelation spectroscopy), is moistened with an aqueous solution of sodium carboxymethylcellulose and sodium dioctylsulphosuccinate and kneaded. The resulting mass is granulated, dried and sieved, and the granulate obtained is mixed with microcrystalline cellulose, talc and magnesium stearate. The powder is filled into size 0 capsules.

Example B

Tablets can be produced as follows:

| Ingredient | mg/tablet |
| --- | --- |
| 1. Compound I as a finely milled powder | 20 |
| 2. Powd. lactose | 100 |
| 3. White corn starch | 60 |
| 4. Povidone K30 | 8 |
| 5. White corn starch | 112 |
| 6. Talc | 16 |
| 7. Magnesium stearate | 4 |
| Total | 320 |

The finely milled substance is mixed with lactose and a portion of the corn starch. The mixture is moistened with an aqueous solution of Povidone K30 and kneaded, and the resulting mass is granulated, dried and sieved. The granulate is mixed with the remaining corn starch, talc and magnesium stearate and pressed to tablets of suitable size.

Example C

Soft gelatine capsules can be produced as follows:

| Ingredient | mg/capsule |
| --- | --- |
| 1. Compound I | 5 |
| 2. Triglyceride | 450 |
| Total | 455 |

10 g of compound I are dissolved in 90 g of medium-chain triglyceride while stirring and with inert gasification and protection from light. This solution is processed as a capsule fill mass to soft gelatine capsules containing 5 mg of active ingredient.

Example D

A cream can be produced in a manner known per se from the constituents listed hereinafter:

| | Wt. % |
| --- | --- |
| Compound of formula I | 0.1–5 |
| Cetyl alcohol | 5.25–8.75 |
| Arlacel 165 (glyceryl/PEG 100 stearate) | 3.75–6.25 |
| Miglyol 818 (caprylic/capric/linoleic acid triglyceride) | 11.25–18.75 |
| Sorbitol solution | 3.75–6.25 |
| Na$_2$ EDTA | 0.075–0.125 |
| Carbopol 934P (carbomer 934P) | 0.15–0.25 |
| Butylated hydroxyanisole | 0.0375–0.0625 |
| Methylparaben | 0.135–0.225 |
| Propylparaben | 0.0375–0.0625 |
| NaOH (10% solution) | 0.15–0.25 |
| Water q.s. | 100.00 |

Example E

A gel can be produced in a manner known per se from the constituents listed hereinafter:

| | Wt. % |
| --- | --- |
| Compound of formula I | 0.1–5 |
| Pluronic L 101 (poloxamer 331) | 10.00 |
| Aerosil 200 (silicon dioxide) | 8.00 |
| PCL liquid (fatty acid ester) | 15.00 |
| Cetiol V (decyl oleate) | 20.00 |
| Neobee oil (medium chain length triglyceride) | 15.00 |
| Euhanol G (octyldodecanol), q.s. | 100.00 |

The physical properties of the preparations can be altered by varying the ratio between the adjuvants in Examples D and E.

We claim:
1. A compound of the formula

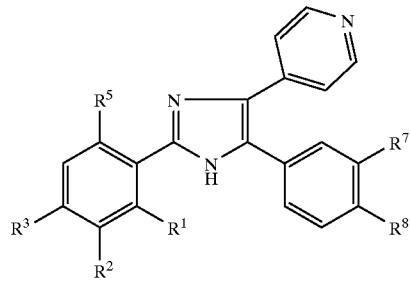

wherein $R^1$ signifies $C_{1-6}$-alkyl or halogen, $R^2$ signifies hydrogen, hydroxy, nitro, $C_{1-6}$-alkoxycarbonyl, di($C_{1-6}$-alkyl)amino-$C_{1-6}$-alkyl, morpholino-$C_{1-6}$-alkyl or 4-methylpiperazinyl-$C_{1-6}$-alkyl, $R^3$ signifies hydrogen or $C_{1-6}$-alkyl, $R^5$ signifies amino or $C_{1-6}$-alkyl, $R^7$ signifies hydrogen or $C_{1-6}$-alkyl and $R^8$ signifies hydrogen or halogen, or a pharmaceutically usable salt thereof.

2. A compound as claimed in claim 1 which is 4-[5-(4-chlorophenyl) -2-(2,4,6-trimethylphenyl)imidazol-4-yl]pyridine.

3. A compound as claimed in claim 1 which is 4-[5-(3-methylphenyl) -2-(2,4,6-trimethylphenyl)imidazol-4-yl]pyridine.

4. A compound as claimed in claim 1 which is 3-chloro-2-[4-(4-chlorophenyl)-5-pyridin-4-yl-imidazol-2-yl]phenylamine.

5. A compound as claimed in claim 1 which is 4-[5-(4-chlorophenyl)-2-(2,6-diisopropylphenyl)imidazol-4-yl]pyridine.

6. A compound as claimed in claim 1 which is methyl 3-[5-(4-chlorophenyl)-4-pyridin-4-yl-imidazol-2-yl]-2,4,6-trimethylbenzoate.

7. A compound as claimed in claim 1 which is 4-[3-[5-(4-chlorophenyl)-4-pyridin-4-yl-imidazol-2-yl]-2,4,6-trimethylbenzyl]morpholine.

8. A compound as claimed in claim 1 which is [3-[5-(4-chlorophenyl)-4-pyridin-4-yl-imidazol-2-yl]-2,4,6-trimethyl-benzyl]dimethylamine.

9. A compound as claimed in claim 1 which is 1-[3-[5-(4-chlorophenyl)-4-chlorophenyl)-4-pyridin-4-yl-imidazol-2-yl]-2,4,6-trimethylbenzyl]-4-methylpiperazine.

10. A compound as claimed in claim 1 which is 4-[5-(4-(chlorophenyl)-2-(2,4,6-trimethyl-3-nitrophenyl)imidazol-4-yl]-pyridine.

11. A compound as claimed in claim 1 which is 3-[5-(4-(4-chlorophenyl)-4-pyridin-4-yl-imidazol-2-yl]-2,4,6-trimethyl-phenol.

12. A compound as claimed in claim 1 which is 4-[5-(4-fluorophenyl)-2-(2-bromo-6-methylphenyl)-imidazol-4-yl]-pyridine.

13. A compound as claimed in claim 1 which is
4-[5-(4-fluorophenyl)-2-(2,4,6-trimethylphenyl)imidazol-4-yl]pyridine,
4-[5-(4-chlorophenyl)-2-(2,6-dimethylphenyl)imidazol-4-yl]pyridine,
4-[5-(4-chlorophenyl)-2-(2-chloro-6-methylphenyl)-imidazol-4-yl]pyridine, 4-[5-(4-chlorophenyl)-2-(2-bromo-6-methylphenyl)-imidazol-4-yl]pyridine, 4-[5-(4-chlorophenyl)-2-(2,6-dimethyl-3-nitrophenyl)-imidazol-4-yl]pyridine, 3-[5-(4-chlorophenyl)-4-pyridin-4-yl-imidazol-2-yl]-2,4-dimethylphenol or (2RS,6RS)- and (2R,6S)-4-[3-[5-(4-chlorophenyl)-4-pyridin- 4-yl-imidazol-2-yl]-2,4,6-trimethylbenzyl]-2,6-dimethylmorpholine.

14. A pharmaceutical composition comprising an effective amount of a compound of the formula

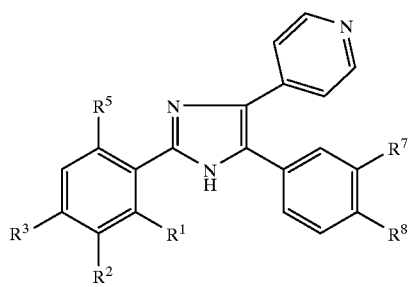

wherein $R^1$ signifies $C_{1-6}$-alkyl or halogen, $R^2$ signifies hydrogen, hydroxy, nitro, $C_{1-6}$-alkoxycarbonyl, di($C_{1-6}$-alkyl)amino-$C_{1-6}$-alkyl, morpholino-$C_{1-6}$-alkyl or 4-methylpiperazinyl-$C_{1-6}$-alkyl, $R^3$ signifies hydrogen or $C_{1-6}$-alkyl, $R^5$ signifies amino or $C^{1-6}$-alkyl, $R^7$ signifies hydrogen or $C_{1-6}$-alkyl and $R^8$ signifies hydrogen or halogen, or a pharmaceutically usable salt thereof and a usual pharmaceutical carrier.

15. A process for the manufacture of compounds set forth in claim 1, which process comprises reacting a diketone of the general formula

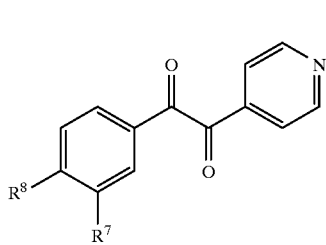

(II)

wherein $R^7$ and $R^8$ have the significance given in claim 1, with an aldehyde of the general formula

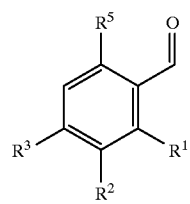

(III)

wherein $R^1$, $R^2$, $R^3$ and $R^5$ have the significance given in claim 1 and wherein a hydroxy group in a compound of formula III can be present in protected form, in the presence of ammonia, and cleaving off a hydroxy protecting group which may be present.

16. A method for the treatment of athersclerosis comprising administering to a host in need of such treatment an effective amount of a compound of the formula

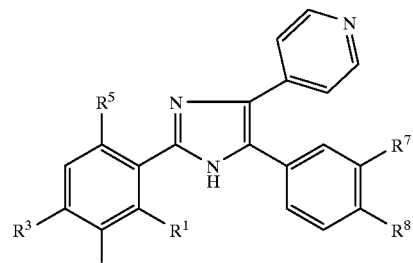

wherein $R^1$ signifies $C_{1-6}$-alkyl or halogen, $R^2$ signifies hydrogen, hydroxy, nitro, $C_{1-6}$-alkoxycarbonyl, di($C_{1-6}$-alkyl)amino-$C_{1-6}$-alkyl, morpholino-$C_{1-6}$-alkyl or 4-methylpiperazinyl-$C_{1-6}$-alkyl, $R^3$ signifies hydrogen or $C_{1-6}$-alkyl, $R^5$ signifies amino or $C_{1-6}$-alkyl, $R^7$ signifies or a pharmaceutically usable salt thereof.

17. A method for the treatment of psoriasis comprising administering to a host in need of such treatment an effective amount of a compound of the formula

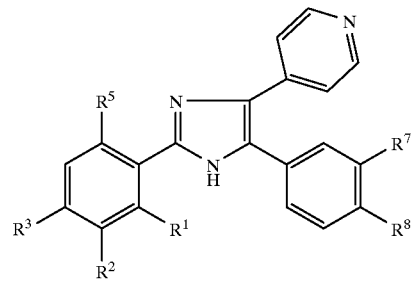

wherein $R^1$ signifies $C_{1-6}$-alkyl or halogen, $R^2$ signifies hydrogen, hydroxy, nitro, $C_{1-6}$-alkoxycarbonyl, di($C_{1-6}$-alkyl)amino-$C_{1-6}$-alkyl, morpholino-$C_{1-6}$-alkyl or 4-methylpiperazinyl-$C_{1-6}$-alkyl, $R^3$ signifies hydrogen or $C_{1-6}$-alkyl, $R^5$ signifies amino or $C_{1-6}$-alkyl, $R^7$ signifies hydrogen or $C_{1-6}$-alkyl and $R^8$ signifies hydrogen or halogen, or a pharmaceutically usable salt thereof.

18. A method for the treatment or prophylaxis of tumors comprising administering to a host in need of such treatment an effective amount of a compound of the formula

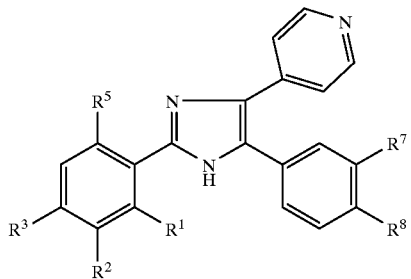

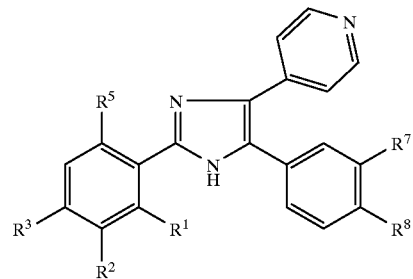

wherein R[1] signifies $C_{1-6}$-alkyl or halogen, R[2] signifies hydrogen, hydroxy, nitro, $C_{1-6}$-alkoxycarbonyl, di($C_{1-6}$-alkyl)amino-$C_{1-6}$-alkyl, morpholino-$C_{1-6}$-alkyl or 4-methylpiperazinyl-$C_{1-6}$-alkyl, R[3] signifies hydrogen or $C_{1-6}$-alkyl, R[5] signifies amino or $C_{1-6}$-alkyl, R[7] signifies hydrogen or $C_{1-6}$-alkyl and R[8] signifies hydrogen or halogen, or a pharmaceutically usable salt thereof.

19. A method for the treatment of alopecia comprising administering to a host in need of such prophylaxis or treatment an effective amount of a compound of the formula wherein R[1] signifies $C_{1-6}$-alkyl or halogen, R[2] signifies hydrogen, hydroxy, nitro, $C_{1-6}$-alkoxycarbonyl, di($C_{1-6}$-alkyl)amino-$C_{1-6}$-alkyl, morpholino-$C_{1-6}$-alkyl or 4-methylpiperazinyl-$C_{1-6}$-alkyl, R[3] signifies hydrogen or $C_{1-6}$-alkyl, R[5] signifies amino or $C_{1-6}$-alkyl, R[7] signifies hydrogen or $C_{1-6}$-alkyl and R[8] signifies hydrogen or halogen, or a pharmaceutically usable salt thereof.

\* \* \* \* \*

UNITED STATES PATENT AND TRADEMARK OFFICE
CERTIFICATE OF CORRECTION

PATENT NO. : 5,959,113
DATED : September 28, 1999
INVENTOR(S) : Harmon, et al.

It is certified that error appears in the above-indentified patent and that said Letters Patent is hereby corrected as shown below:

COVER PAGE: Item [54] and column 1,

The Title information should read —IMIDAZOLE DERIVATIVES AS PROTEIN KINASE INHIBITORS IN PARTICULAR EGF-R TYROSINE KINASE—.

IN THE CLAIMS:

Claim 9, Column 12, line 48: in the second instance "-4-chlorophenyl)" should be deleted.

Claim 11, Column 12, lines 54-55: "3-[5-(4-(4-chlorophenyl)" should read — 3-[5-(4-chlorophenyl) —.

UNITED STATES PATENT AND TRADEMARK OFFICE
CERTIFICATE OF CORRECTION

PATENT NO. : 5,959,113
DATED : September 28, 1999
INVENTOR(S) : Harmon, et al.

It is certified that error appears in the above-identified patent and that said Letters Patent is hereby corrected as shown below:

Claim 14, Column 13, line 29: "$C^{1-6}$" should read -- $C_{1-6}$ --.

Claim 18, Column 14, line 61: "or prophylaxis" should be deleted.

Claim 19, Column 15, line 24: "prophylaxis or" should be deleted.

Signed and Sealed this

Second Day of May, 2000

Attest:

Q. TODD DICKINSON

Attesting Officer

Director of Patents and Trademarks